United States Patent [19]

Levitt

[11] 4,214,890

[45] Jul. 29, 1980

[54] HERBICIDAL PYRIMIDINE AND TRIAZINE SULFONAMIDES

[75] Inventor: George Levitt, Wilmington, Del.

[73] Assignee: E. I. Du Pont de Nemours and Company, Wilmington, Del.

[21] Appl. No.: 946,176

[22] Filed: Sep. 27, 1978

[51] Int. Cl.$^2$ .............................................. A01N 9/12
[52] U.S. Cl. ....................................... 71/90; 71/92; 71/93; 544/212; 544/320; 544/321
[58] Field of Search ..................... 544/212, 320, 321; 71/90, 92, 93

[56] References Cited

FOREIGN PATENT DOCUMENTS 1468747  2/1967  France .
 121788  9/1966  Netherlands .

OTHER PUBLICATIONS

Logemann et al, Chem. Abs., 53, 18052 g (1959).
J. Drug Res., 6, 123 (1974).
Wojciechowski, J. Acta. Pol. on Pharm., 19, pp. 121–125 (1962).

Primary Examiner—Anton H. Sutto
Assistant Examiner—Lisa Jones

[57] ABSTRACT

N-(heterocyclicaminocarbonyl)arylsulfonamides and thienylsulfonamides in which the heterocyclic radical is substituted in one position by a methyl or methoxy radical and in another by a substituted alkoxy or alkylthio radical; e.g., N-[[4-(2-methoxyethoxy)-6-methylpyrimidin-2-yl]aminocarbonyl]-2-nitrobenzenesulfonamide and N-[[4-(2,2,2-trifluoroethoxy)-6-methylpyrimidin-2-yl]aminocarbonyl]-2-nitrobenzenesulfonamide; are useful for the regulation of plant growth and as pre-emergence and post-emergence herbicides.

27 Claims, No Drawings

HERBICIDAL PYRIMIDINE AND TRIAZINE SULFONAMIDES

BACKGROUND OF THE INVENTION

This invention relates to novel N-(heterocyclicaminocarbonyl)arylsulfonamides and N-(heterocyclicaminocarbonyl)thienylsulfonamides in which the heterocyclic radical is substituted in one position by a methyl or methoxy radical and in another by a substituted alkoxy or alkylthio radical. The compounds of this invention and their agriculturally suitable salts, are useful as agricultural chemicals, e.g., plant growth regulants and herbicides.

U.S. application Ser. Nos. 824,805 filed Aug. 15, 1977 and 840,389, filed Oct. 6, 1977 disclose, inter alia, compounds of the following formula as herbicides:

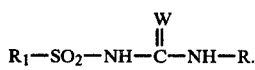

In the former R is a radical having the formula:

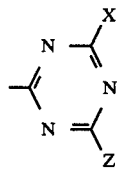

and in the latter, a radical having the formula:

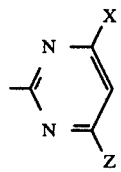

In each of those applications,
R₁ may be

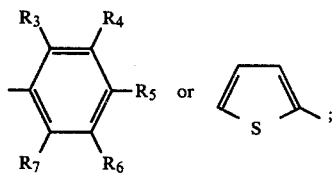

R₃ may be chlorine, bromine, fluorine, nitro, methyl, methoxy, trifluoromethyl or

n is 0, 1 or 2;

R₄, R₅, R₆ and R₇ may each be hydrogen, fluorine, chlorine, bromine, or methyl; moreover in each application, each of R₅, R₆ and R₇ may be methoxy. In each application, X may be alkoxy of 1-3 carbon atoms, trifluoromethyl, CH₃S— or CH₃OCH₂—; Z is methyl or methoxy; and W is oxygen or sulfur.

U.S. application Ser. No. 840,167, filed Oct. 6, 1977, discloses, inter alia, compounds having the following formula as herbicides:

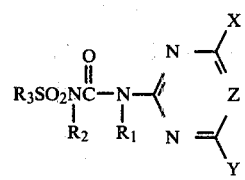

wherein
each of R₁ and R₂ may be hydrogen or methyl;
R₃ is

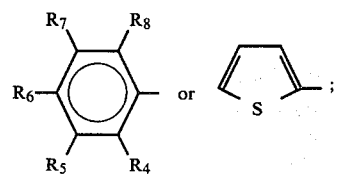

X may be alkoxy of one to three carbons, CF₃, CH₃S—, CH₃OCH₂— or CH₃OCH₂CH₂O—;
Y is CH₃ or OCH₃; and
Z is CH or N.

U.S. application Ser. No. 910,965, filed May 30, 1978, discloses, inter alia, compounds of the following formula as herbicides:

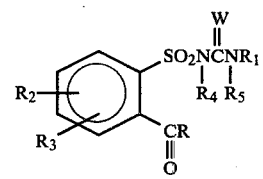

wherein $$-\underset{O}{\overset{\|}{C}}R$$

is an acid, salt, ester or amide radical;
R₁ may be

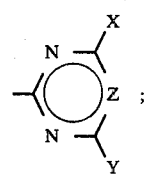

R₂ may be hydrogen, chlorine, bromine, fluorine, nitro, methyl, methoxy or methylthio; R₃ is hydrogen, chlorine, bromine or methyl;
R₄ and R₅ are independently hydrogen or methyl;
W is oxygen or sulfur;
X may be methyl or methoxy;
Y may be —OCH₂CF₃, —O(CH₂)₂OCH₃, —O(CH₂)₂OC₂H₅, —O(CH₂)₃OCH₃, —O(CH₂)₃OC₂H₅, —OCH₂CO₂CH₃, —OCH₂CO₂C₂H₅, $$-\underset{\underset{CH_3}{|}}{O}CHCO_2CH_3, \quad -\underset{\underset{CH_3}{|}}{O}CHCO_2C_2H_5,$$

—O(CH$_2$)$_2$CO$_2$CH$_3$, —O(CH$_2$)$_2$CO$_2$C$_2$H$_5$; —S(CH$_2$)$_2$OCH$_3$, —S(CH$_2$)$_2$OC$_2$H$_5$, —SCH$_2$CO$_2$CH$_3$, —SCH$_2$CO$_2$C$_2$H$_5$, $$-\underset{\underset{CH_3}{|}}{S}CHCO_2CH_3, \quad -\underset{\underset{CH_3}{|}}{S}CHCO_2C_2H_5,$$

—S(CH$_2$)$_2$CO$_2$CH$_3$, or S(CH$_2$)$_2$CO$_2$C$_2$H$_5$; and Z is CH or N.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth of undesired vegetation is one way of improving this efficiency. A wide variety of materials useful for killing or inhibiting (controlling) the growth of undesired vegetation is available; such materials are commonly referred to as herbicides. However, the need still exists for effective herbicides.

SUMMARY OF THE INVENTION

According to this invention, there are provided novel compounds of Formula I and their agriculturally suitable salts, suitable agricultural compositions containing them and methods of using them as plant growth regulants pre-emergence and post-emergence herbicides, both general and selective:

$$RSO_2\underset{\underset{R_1}{|}}{N}\underset{\underset{R_2}{|}}{C}N\underset{}{\overset{W}{\|}}\text{—pyrimidine/triazine ring with X, Z, N, YR}_3 \quad (I)$$

wherein
R is

[thiophene] or [benzene with R$_5$, R$_4$ substituents]

R$_1$ and R$_2$ are independently H or CH$_3$;
R$_3$ is —CH$_2$CF$_3$, —CH$_2$CH$_2$OR$_6$, —CH$_2$CO$_2$R$_6$, $$-\underset{\underset{CH_3}{|}}{C}HCO_2R_6,$$

—CH$_2$CH$_2$—CH$_2$OR$_6$ or —CH$_2$CH$_2$CO$_2$R$_6$;
R$_4$ is Cl, Br, F, NO$_2$, CH$_3$, —OCH$_3$, CF$_3$, or $$-\underset{\underset{(O)_n}{|}}{S}CH_3;$$

R$_5$ is H, Cl, Br, F, CH$_3$ or —OCH$_3$;
R$_6$ is CH$_3$ or CH$_2$CH$_3$;
n is 0, 1 or 2;
X is CH$_3$ or —OCH$_3$;
W and Y are independently O or S; and
Z is CH or N;
provided that when
(a) R$_3$ is —CH$_2$CF$_3$, Y is O; and
(b) R$_3$ is —CH$_2$CH$_2$OCH$_3$ and either or both of R$_1$ and R$_2$ is CH$_3$, Y is S.

Preferred in order of increasing activity and/or increasingly favorable cost are:

(1) Compounds of the generic scope wherein R$_1$ and R$_2$ are H and W is O;
(2) Compounds of preference (1) wherein R is

[benzene with R$_5$, R$_4$ substituents];

(3) Compounds of preference (2) wherein R$_5$ is H or Cl;
(4) Compounds of preference (3) wherein R$_4$ is Cl or NO$_2$;
(5) Compounds of preference (4) wherein R$_5$ is H.

More preferred in order of increasing activity and/or increasingly more favorable cost are:
(6) Compounds of the generic scope wherein Y is O;
(7) Compounds of preference (1) wherein Y is O;
(8) Compounds of preference (2) wherein Y is O;
(9) Compounds of preference (3) wherein Y is O;
(10) Compounds of preference (4) wherein Y is O;
(11) Compounds of preference (5) wherein Y is O.

Specifically preferred for their exceptional activity and/or very favorable cost are:
N-[[4-(2-methoxyethoxy)-6-methylpyrimidin-2-yl]aminocarbonyl]-2-nitrobenzenesulfonamide,
N-[[4-(2,2,2-trifluoroethoxy)-6-methylpyrimidin-2-yl]aminocarbonyl]-2-nitrobenzenesulfonamide.

Synthesis

As shown in Equation 1, the compounds of Formula I can be prepared by reacting an appropriately substituted sulfonyl isocyanate or isothiocyanate of Formula II with an appropriate 2-aminopyrimidine or 2-amino-1,3,5-triazine of Formula III; R$_2$, R$_3$, W, X, Y and Z being as previously defined.

Equation 1.

RSO$_2$NCW + (II)

[H$_2$N—pyrimidine/triazine ring with X, Z, N, YR$_3$] → (III)

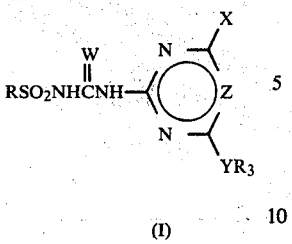
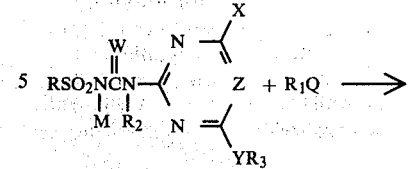

(I)

The reaction of Equation 1 is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate II to a stirred suspension of heterocyclic amine III. Since such isocyanates and isothiocyanates usually are liquids, their addition can be easily controlled. The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

As shown in Equation 2, the compounds of Formula I, wherein $R_1$ is H and $R_2$ is $CH_3$, can be prepared by reacting an appropriately substituted sulfonyl isocyanate or isothiocyanate of Formula II with an appropriate 2-methylaminopyrimidine or 2-methylamino-1,3,5-triazine of Formula III; R, $R_3$, W, X, Y and Z being as previously defined.

Equation 2

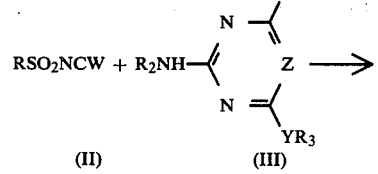

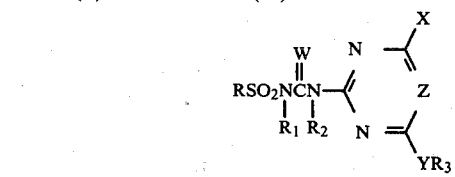

(I)

The reaction is carried out as is described for that of Equation 1.

Compounds of Formula I wherein $R_1$ is methyl, can be prepared by methylation of the salts of compounds of Formula I wherein $R_1$ is H, as shown in Equation 3; R, $R_2$, $R_3$, W, X, Y and Z being as previously defined and M is a metal cation and Q an anion, such as halide or sulfate.

Equation 3

The reaction of Equation 3 is best carried out in aprotic organic solvents such as tetrahydrofuran, dimethylformamide, or dimethylacetamide, at ambient pressure and temperature. Alkylating agents such as dimethyl sulfate, or methyl iodide can be employed. The desired product can be isolated by pouring the reaction mixture into water and filtering off the precipitated solid.

Alternatively, compounds of Formula I wherein $R_1$ is methyl, can be prepared by the reaction of an appropriately substituted sulfonyl-N-methylcarbamyl chloride or sulfonyl-N-methylcarbamylthioic chloride of Formula IV with an appropriate 2-aminopyrimidine or 2-amino-1,3,5-triazine of Formula III; as shown in Equation 4; $R_2$, $R_1$, R, X, Y, and Z being as previously defined.

Equation 4

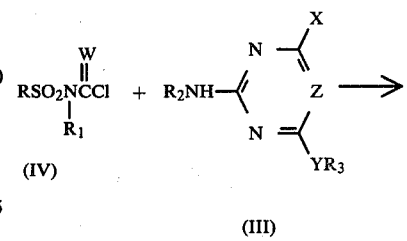

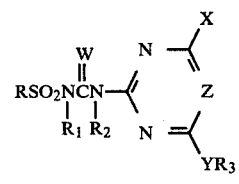

(I)

The preparation of ureas from amines and carbamyl chlorides or carbamylthioic chlorides is well known to the art. The reaction can best be carried out by adding equivalent amounts of the chloride IV and amine III to an inert organic solvent, such as tetrahydrofuran, xylene, or methylene chloride, in the presence of acid acceptor, such as triethylamine, pyridine, or sodium carbonate employing temperatures from 20°–130°. Soluble products can be isolated by filtering off precipitated salts and concentration of the filtrate. Insoluble products can be filtered off and washed free of salts with water.

The intermediate chlorides IV can be prepared by phosgenation or thiophosgenation of N-methylsulfonamide salts. The sulfonamide salt is added to an excess of phosgene or thiophosgene in an inert organic solvent, such as tetrahydrofuran, toluene, or xylene, whereupon the chloride IV can be isolated or reacted in situ with the amine III after removal of the excess phosgene or thiophosgene.

The preparation of agriculturally suitable salts of the compounds of Formula I, as well as starting materials and intermediates for said compounds is disclosed in U.S. applications Ser. No. 824,805 filed Aug. 15, 1977 and Ser. No. 840,389 filed Oct 6, 1977, the contents of which are incorporated herein by reference.

The compounds of this invention and their preparation are further illustrated by the following examples wherein temperatures are given in degrees centigrade.

EXAMPLE 1

N-[[4-(2-methoxyethoxy)-6-methylpyrimidin-2-yl]aminocarbonyl]-2-chlorobenzenesulfonamide To a dry stirred solution of 18.3 parts of 2-amino-4-(2-methoxyethoxy)-6-methylpyrimidine in 300 parts of methylene chloride at ambient temperature and pressure was added 22 parts of 2-chlorobenzenesulfonylisocyanate. The mixture was stirred for 2 hours and then the methylene chloride was removed under reduced pressure. The resulting solid was triturated with 1-chlorobutane and filtered to yield 35 parts of N-[[4-(2-methoxyethoxy)-6-methylpyrimidine-2-yl]aminocarbonyl]-2-chlorobenzenesulfonamide, m.p. 130°–140° C. The product showed characteristic absorption bands in the infrared spectrum.

By using the procedure of Example 1 with an equivalent amount of appropriate 2-aminopyrimidines or 2-amino-1,3,5-triazines and appropriately substituted benzenesulfonyl isocyanates or isothiocyanates, the compounds of Table 1 can be prepared.

Table 1-A

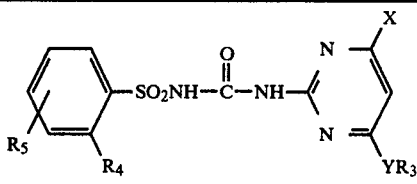

| $R_4$ | $R_5$ | X | $YR_3$ | m.p. °C. |
|---|---|---|---|---|
| Cl | H | $CH_3$ | $OCH_2CH_2OC_2H_5$ | |
| Cl | H | $CH_3$ | $OCH_2CF_3$ | 160–163 |
| Cl | H | $CH_3$ | $OCH_2CO_2CH_3$ | 157–160 |
| Cl | H | $CH_3$ | $OCH_2CO_2C_2H_5$ | |
| Cl | H | $CH_3$ | $OCHCO_2CH_3$<br>\|<br>$CH_3$ | 178–191 |
| Cl | H | $CH_3$ | $O-CHCO_2C_2H_5$<br>\|<br>$CH_3$ | 114–122 |
| Cl | H | $CH_3$ | $O-CH_2CH_2CO_2CH_3$ | |
| Cl | H | $CH_3$ | $OCH_2CH_2CO_2C_2H_5$ | |
| Cl | H | $CH_3$ | $OCH_2CH_2CH_2OCH_3$ | 103–115 |
| Br | H | $CH_3$ | $OCH_2CH_2OCH_3$ | |
| Br | H | $CH_3$ | $OCH_2CF_3$ | |
| Br | H | $CH_3$ | $OCH_2CO_2CH_3$ | |
| F | H | $CH_3$ | $OCH_2CH_2OC_2H_5$ | |
| F | H | $CH_3$ | $OCH_2CF_3$ | |
| F | H | $CH_3$ | $OCH_2CO_2CH_3$ | |
| $NO_2$ | H | $CH_3$ | $OCH_2CH_2CH_2OCH_3$ | |
| $NO_2$ | H | $CH_3$ | $OCH_2CH_2OCH_3$ | 95–98 |
| $NO_2$ | H | $CH_3$ | $OCH_2CH_2OC_2H_5$ | |
| $NO_2$ | H | $CH_3$ | $OCH_2CF_3$ | 192–194 |
| $NO_2$ | H | $CH_3$ | $OCH_2CO_2CH_3$ | 155–165 |
| $NO_2$ | H | $CH_3$ | $OCH_2CO_2C_2H_5$ | |
| $NO_2$ | H | $CH_3$ | $OCHCO_2CH_3$<br>\|<br>$CH_3$ | 175–179 |
| $NO_2$ | H | $CH_3$ | $O-CHCO_2C_2H_5$<br>\|<br>$CH_3$ | |
| $NO_2$ | H | $CH_3$ | $O-CH_2CH_2CO_2CH_3$ | |
| $NO_2$ | H | $CH_3$ | $OCH_2CH_2CO_2C_2H_5$ | |
| $NO_2$ | H | $CH_3$ | $OCH_2CH_2CH_2OC_2H_5$ | |
| $CH_3$ | H | $CH_3$ | $OCH_2CH_2OCH_3$ | |
| $CH_3$ | H | $CH_3$ | $OCH_2CF_3$ | |
| $CH_3$ | H | $CH_3$ | $OCH_2CO_2C_2H_5$ | |
| $CH_3$ | H | $CH_3$ | $OCHCO_2CH_3$<br>\|<br>$CH_3$ | |
| $CH_3$ | H | $CH_3$ | $OCH_2CH_2CO_2C_2H_5$ | |
| $OCH_3$ | H | $CH_3$ | $OCH_2CH_2OC_2H_5$ | |
| $OCH_3$ | H | $CH_3$ | $OCH_2CF_3$ | |
| $OCH_3$ | H | $CH_3$ | $OCH_2CO_2CH_3$ | |
| $OCH_3$ | H | $CH_3$ | $OCH_2CH_2CO_2CH_3$ | |
| $CF_3$ | H | $CH_3$ | $OCH_2CH_2OCH_3$ | |
| $CF_3$ | H | $CH_3$ | $OCH_2CF_3$ | |
| $CF_3$ | H | $CH_3$ | $CHCO_2C_2H_5$<br>\|<br>$CH_3$ | |
| $CF_3$ | H | $CH_3$ | $OCH_2CH_2CO_2CH_3$ | |
| $SCH_3$ | H | $CH_3$ | $OCH_2CH_2OC_2H_5$ | |
| $SCH_3$ | H | $CH_3$ | $OCH_2CO_2C_2H_5$ | |
| $\overset{O}{\underset{\uparrow}{S}}CH_3$ | H | $CH_3$ | $OCH_2CF_3$ | |
| $\overset{O}{\underset{\uparrow}{S}}CH_3$ | H | $CH_3$ | $OCHCO_2CH_3$<br>\|<br>$CH_3$ | |
| $\overset{O}{\underset{\uparrow}{S}}CH_3$ | H | $CH_3$ | $OCH_2CH_2CO_2C_2H_5$ | |
| $\overset{O}{\underset{\uparrow}{S}}CH_3$ | H | $CH_3$ | $OCH_2CH_2OCH_3$ | |
| $\overset{O}{\underset{\uparrow}{S}}CH_3$ | H | $CH_3$ | $OCH_2CF_3$ | |
| $\overset{O}{\underset{\uparrow}{\underset{\downarrow}{S-CH_3}}}\overset{}{O}$ | H | $CH_3$ | $OCH_2CO_2C_2H_5$ | |
| Cl | 5-Cl | $CH_3$ | $OCH_2CH_2OCH_3$ | 151–155 |
| Cl | 5-Cl | $CH_3$ | $OCH_2CF_3$ | 162.5–165 |
| Cl | 5-Cl | $CH_3$ | $OCH_2CO_2CH_3$ | 182–186 |
| Cl | 5-Cl | $CH_3$ | $OCHCO_2CH_3$<br>\|<br>$CH_3$ | |
| Cl | 5-Cl | $CH_3$ | $OCH_2CH_2CH_2OCH_3$ | |
| Cl | 3-Cl | $CH_3$ | $OCH_2CH_2OCH_3$ | |
| Cl | 5-Br | $CH_3$ | $OCH_2CH_2OC_2H_5$ | |
| Cl | 5-F | $CH_3$ | $OCH_2CF_3$ | |
| Cl | 5-$CH_3$ | $CH_3$ | $OCH_2CO_2CH_3$ | |
| Cl | 5-$OCH_3$ | $CH_3$ | $OCH_2CF_3$ | |
| Cl | 6-Cl | $CH_3$ | $OCH_2CO_2C_2H_5$ | |

Table 1-A-continued

Structure: Phenyl(R4, R5)-SO2NH-C(=O)-NH-[pyrimidine with X at 4-position, YR3 at 6-position]

| R4 | R5 | X | YR3 | m.p. °C |
|---|---|---|---|---|
| Br | 5-Br | CH3 | OCHCO2CH3 (CH3) | |
| Cl | 5-Cl | OCH3 | OCH2CO2C2H5 | |
| Cl | 5-Cl | OCH3 | OCH2CH2OC2H5 | |
| F | 5-F | CH3 | OCH2CH2CO2C2H5 | |
| NO2 | 5-Cl | CH3 | OCH2CH2OCH3 | |
| NO2 | 6-Cl | CH3 | OCH2CO2C2H5 | |
| NO2 | 3-CH3 | CH3 | OCH2CH2OCH3 | |
| NO2 | 5-OCH3 | CH3 | OCH2CF3 | |
| CH3 | 5-OCH3 | CH3 | OCH2CH2OCH3 | |
| CH3 | 5-Cl | CH3 | OCHCO2CH3 (CH3) | |
| OCH3 | 5-OCH3 | CH3 | OCH2CH2OC2H5 | |
| CF3 | 5-Cl | CH3 | OCH2CF3 | |
| CF3 | 5-Cl | CH3 | OCH2CO2CH3 | |
| SCH3 | 5-Cl | CH3 | OCH2CH2OCH3 | |
| S(=O)(=O)CH3 | 5-Cl | CH3 | —OCH2CH2CO2CH3 | |
| S(=O)(=O)CH3 | 5-OCH3 | CH3 | OCH2CF3 | |
| Cl | H | CH3 | SCH2CH2OC2H5 | 127–130 |
| Cl | H | CH3 | SCH2CO2CH3 | |
| Cl | 5-Cl | CH3 | SCH2CH2OC2H5 | 131–150 |
| Cl | 5-Cl | CH3 | SCHCO2CH3 (CH3) | |
| Br | H | CH3 | SCH2CH2OCH3 | |
| F | H | CH3 | SCH2CH2CO2C2H5 | |
| NO2 | H | CH3 | SCH2CH2OC2H5 | |
| NO2 | H | CH3 | SCH2CO2C2H5 | |
| CH3 | H | CH3 | SCH2CH2OCH3 | |
| OCH3 | H | CH3 | SCH2CH2OC2H5 | |
| CF3 | H | CH3 | SCHCO2C2H5 (CH3) | |
| CF3 | 5-Cl | CH3 | S—CH2CH2OCH3 | |
| S(=O)(=O)CH3 | H | CH3 | S—CH2CH2OC2H5 | |
| Cl | H | OCH3 | OCH2CH2OCH3 | |
| Cl | 5-Cl | OCH3 | OCH2CF3 | |
| NO2 | H | OCH3 | OCH2CO2CH3 | |
| CF3 | H | OCH3 | OCH2CH2OC2H5 | |
| CH3 | H | OCH3 | S-CH2CH2OC2H5 | |
| OCH3 | H | OCH3 | OCH2CF3 | |
| S(=O)(=O)CH3 | H | OCH3 | OCH2CH2CO2CH3 | |

Table 1-B

Structure: Phenyl(R4, R5)-SO2NH-C(=O)-NH-[triazine with X and YR3]

| R4 | R5 | X | YR3 |
|---|---|---|---|
| Cl | H | CH3 | OCH2CH2OCH3 |
| Cl | 5-Cl | CH3 | OCH2CF3 |
| NO2 | H | CH3 | OCH2CO2C2H5 |
| NO2 | H | CH3 | OCH2CH2CO2CH3 |
| CH3 | H | CH3 | OCH2CH2OCH3 |
| OCH3 | H | CH3 | OCH2CH2OC2H5 |
| SCH3 | H | CH3 | OCHCO2CH3 (CH3) |
| S(=O)CH3 | H | CH3 | S—CH2CO2CH3 |
| CF3 | H | CH3 | S—CH2CH2OCH3 |
| F | H | OCH3 | OCH2CF3 |
| Br | H | OCH3 | OCH2CH2OCH3 |
| S(=O)(=O)CH3 | H | OCH3 | S—CHCO2C2H5 (CH3) |

Table 1-C

Structure: Phenyl(R4, R5)-SO2NH-C(=S)-NH-[pyrimidine with X, Y]

| R4 | R5 | X | YR3 |
|---|---|---|---|
| Cl | H | CH3 | OCH2CH2OC2H5 |
| Cl | H | CH3 | OCH2CF3 |
| Cl | 5-Cl | CH3 | OCH2CO2C2H5 |
| Cl | 5-Cl | CH3 | OCHCO2CH3 (CH3) |
| NO2 | H | CH3 | OCH2CH2OCH3 |
| NO2 | H | CH3 | OCH2CF3 |
| Br | H | OCH3 | S—CH2CO2CH3 |
| CH3 | H | OCH3 | O—CH2CH2CH2OC2H5 |

Table 1-D

Structure: Phenyl(R4, R5)-SO2NH-C(=S)-NH-[triazine with X, YR3]

| R4 | R5 | X | YR3 |
|---|---|---|---|
| Cl | H | CH3 | OCH2CH2OCH3 |
| Cl | H | CH3 | OCH2CF3 |
| Cl | 5-Cl | CH3 | OCH2CO2CH3 |
| NO2 | H | CH3 | OCHCO2C2H5 (CH3) |
| NO2 | H | CH3 | S—CH2CH2OC2H5 |
| NO2 | H | CH3 | OCH2CH2OC2H5 |
| NO2 | H | OCH3 | OCH2CF3 |
| Br | H | CH3 | OCH2CH2OCH3 |

Table 1-D-continued

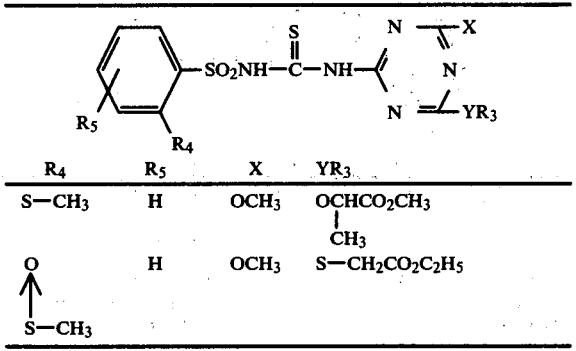

| R4 | R5 | X | YR3 |
|---|---|---|---|
| S—CH3 | H | OCH3 | OCHCO2CH3<br>\|<br>CH3 |
| O<br>↑<br>S—CH3 | H | OCH3 | S—CH2CO2C2H5 |

EXAMPLE 2

Methyl [6-methyl-2-[(2-thienylsulfonyl)aminocarbonylamino]-pyrimidin-4-yloxy]acetate To a dry stirred solution of 18 parts of methyl (2-amino-6-methylpyrimidin-4-yloxy)acetate in 300 parts of methylene chloride at ambient temperature was added 20 parts of 2-thiophenesulfonylisocyanate. The solution was allowed to stand for 3 hours and was then poured onto ice. The pH of the aqueous layer was adjusted to 11 with sodium hydroxide solution and the methylene chloride layer was separated therefrom. The aqueous layer was neutralized with aqueous hydrochloric acid and then extracted with methylene chloride. The extract was dried and stripped of solvent to yield 8 parts of methyl [6-methyl-2-[(2-thienylsulfonyl)aminocarbonylamino]pyrimidin-4-yloxy]acetate, m.p. 114°–120°.

By using the procedure of Example 2 with equivalent amounts of appropriate 2-aminopyrimidines or 2-amino-1,3,5-triazines and 2-thiophenesulfonylisocyanates or isothiocyanates, the compounds of Table 2 can be prepared.

Table 2-A

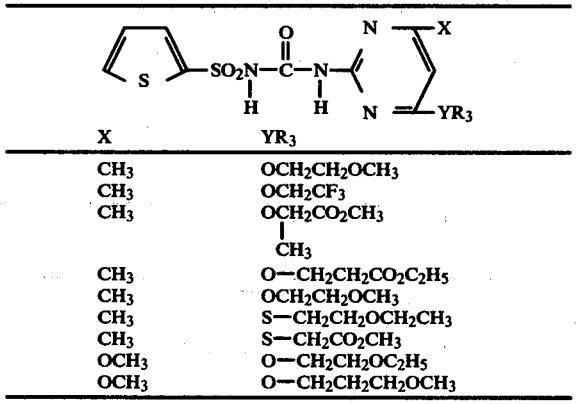

| X | YR3 |
|---|---|
| CH3 | OCH2CH2OCH3 |
| CH3 | OCH2CF3 |
| CH3 | OCH2CO2CH3<br>\|<br>CH3 |
| CH3 | O—CH2CH2CO2C2H5 |
| CH3 | OCH2CH2OCH3 |
| CH3 | S—CH2CH2OCH2CH3 |
| CH3 | S—CH2CO2CH3 |
| OCH3 | O—CH2CH2OC2H5 |
| OCH3 | O—CH2CH2CH2OCH3 |

Table 2-B

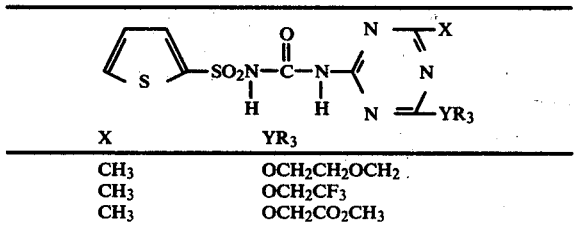

| X | YR3 |
|---|---|
| CH3 | OCH2CH2OCH2 |
| CH3 | OCH2CF3 |
| CH3 | OCH2CO2CH3 |

Table 2-B-continued

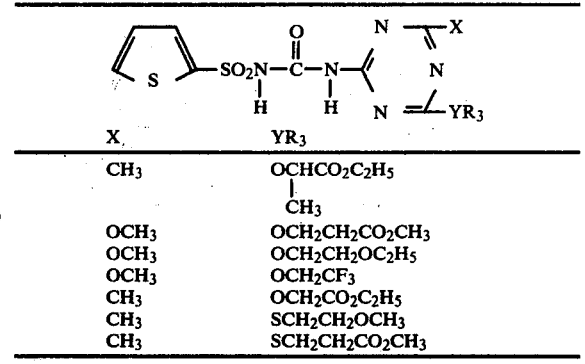

| X | YR3 |
|---|---|
| CH3 | OCHCO2C2H5<br>\|<br>CH3 |
| OCH3 | OCH2CH2CO2CH3 |
| OCH3 | OCH2CH2OC2H5 |
| OCH3 | OCH2CF3 |
| CH3 | OCH2CO2C2H5 |
| CH3 | SCH2CH2OCH3 |
| CH3 | SCH2CH2CO2CH3 |

Table 2-C

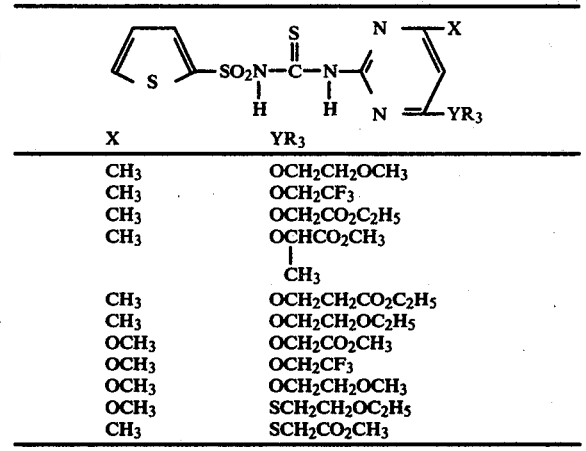

| X | YR3 |
|---|---|
| CH3 | OCH2CH2OCH3 |
| CH3 | OCH2CF3 |
| CH3 | OCH2CO2C2H5 |
| CH3 | OCHCO2CH3<br>\|<br>CH3 |
| CH3 | OCH2CH2CO2C2H5 |
| CH3 | OCH2CH2OC2H5 |
| OCH3 | OCH2CO2CH3 |
| OCH3 | OCH2CF3 |
| OCH3 | OCH2CH2OCH3 |
| OCH3 | SCH2CH2OC2H5 |
| CH3 | SCH2CO2CH3 |

Table 2-D

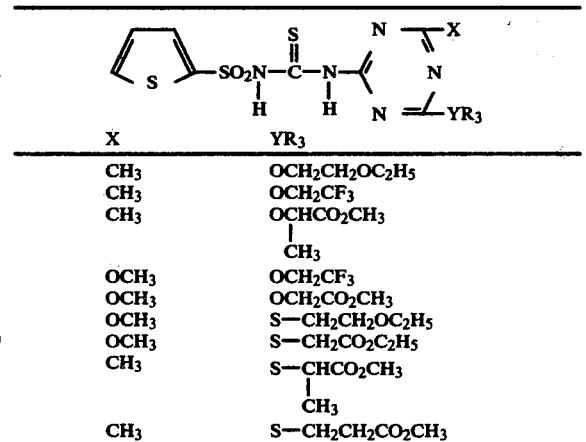

| X | YR3 |
|---|---|
| CH3 | OCH2CH2OC2H5 |
| CH3 | OCH2CF3 |
| CH3 | OCHCO2CH3<br>\|<br>CH3 |
| OCH3 | OCH2CF3 |
| OCH3 | OCH2CO2CH3 |
| OCH3 | S—CH2CH2OC2H5 |
| OCH3 | S—CH2CO2C2H5 |
| CH3 | S—CHCO2CH3<br>\|<br>CH3 |
| CH3 | S—CH2CH2CO2CH3 |

By using the procedure of Equation 2 with an equivalent amount of appropriate 2-methylaminopyrimidines or 2-methylamino-1,3,5-triazines and appropriately substituted benzenesulfonylisocyanates or isothiocyanates, the compounds of Table 3 can be prepared. For example, to a dry stirred solution of 19.7 parts of 2-methylamino-4-(2-methoxyethylthio)-6-methylpyrimidine in 300 parts of methylene chloride at ambient temperature is added 22.8 parts of 2-nitrobenzenesulfonylisocyanate. That mixture is stirred and refluxed for 4 hours, and then the methylene chloride is removed under reduced pressure. The resulting solid is triturated with 1-chlorobutane to yield N-[N-[4-(2-methoxyethylthio)-6-methylpyrimidin-2-yl]-N-methylaminocarbonyl]-2-nitrobenzenesulfonamide.

Table 3-A

| R4 | R5 | X | YR3 |
|---|---|---|---|
| Cl | H | CH3 | SCH2CH2OCH3 |
| Cl | H | CH3 | OCH2CF3 |
| Cl | 5-Cl | CH3 | OCH2CO2CH3 |
| NO2 | H | CH3 | OCH2CH2CO2C2H5 |
| NO2 | H | OCH3 | S—CH2CH2OC2H5 |
| Br | H | CH3 | S—CH2CO2CH3 |
| CH3 | H | CH3 | O—CH—CO2CH3<br>\|<br>CH3 |

Table 3-B

| R4 | R5 | X | YR3 |
|---|---|---|---|
| Cl | H | CH3 | SCH2CH2OC2H5 |
| Cl | H | CH3 | OCH2CF3 |
| Cl | 5-Cl | CH3 | S—CH2CH2OC2H5 |
| NO2 | H | CH3 | OCH2CO2C2H5 |
| Br | H | CH3 | OCH2CH2CO2CH3 |
| OCH3 | H | OCH3 | OCH2CF3 |

Table 3-C

| R4 | R5 | X | YR3 |
|---|---|---|---|
| Cl | H | CH3 | SCH2CH2OCH3 |
| Cl | H | CH3 | OCH2CO2C2H5 |
| Cl | 5-Cl | CH3 | OCH2CH2CH2OCH3 |
| NO2 | H | CH3 | OCH2CF3 |
| NO2 | H | OCH3 | OCH2CF3 |

Table 3-D

| R4 | R5 | X | YR3 |
|---|---|---|---|
| Cl | H | CH3 | OCH2CH2OC2H5 |
| Cl | H | CH3 | OCHCO2CH3<br>\|<br>CH3 |
| Cl | 5-Cl | OCH3 | OCH2CF3 |
| NO2 | H | CH3 | S—CH2CH2OC2H5 |
| NO2 | H | OCH3 | O—CH2CH2CO2C2H5 |
| Br | H | CH3 | OCH2CF3 |

EXAMPLE 3

N-[N-[4-(2,2,2-Trifluoroethoxy)-6-methylpyrimidin-2-yl]-N-methylaminocarbonyl]-2-thiophenesulfonamide To a dry stirred solution of 22.1 parts of 2-methylamino-4-(2,2,2-trifluoroethoxy)-6-methylpyrimidine in 250 parts of methylene chloride at ambient temperature was added 18.9 parts of 2-thiophenesulfonyl isocyanate. That mixture was stirred and refluxed for 2 hours. The methylene chloride was removed under reduced pressure, and the resulting solid was triturated with toluene to yield 19 parts of N-[N-[4-(2,2,2-trifluoroethoxy)-6-methylpyrimidin-2-yl]-N-methylaminocarbonyl]-2-thiophenesulfonamide.

By using the procedure of Example 3 with equivalent amounts of appropriate 2-methylaminopyrimidines or 2-methylamino-1,3,5-triazines and 2-thiophenesulfonyl isocyanates or isothiocyanates, the compounds of Table 4 can be prepared.

Table 4-A

| X | YR3 |
|---|---|
| CH3 | SCH2CH2OCH3 |
| CH3 | OCH2CO2CH3 |
| CH3 | OCH2CH2CO2CH3 |
| CH3 | —S—CH2CH2OC2H5 |
| OCH3 | OCH2CH2OC2H5 |
| OCH3 | OCH2CF3 |
| OCH3 | OCH—CO2CH3<br>\|<br>CH3 |

Table 4-B

| X | YR3 |
|---|---|
| CH3 | OCH2CH2OC2H5 |
| CH3 | OCH2CF3 |
| CH3 | OCH2CH2CH2OCH3 |
| OCH3 | S—CH2CH2CH2OC2H5 |
| OCH3 | S—CH2CO2C2H5 |

Table 4-C

| X | YR3 |
|---|---|
| CH3 | SCH2CH2OCH3 |
| CH3 | OCH2CF3 |
| CH3 | OCH2CH2CO2CH3 |
| OCH3 | S—CH2CH2OC2H5 |

Table 4-D

[Structure: thiophene-SO₂NHC(=S)-N(CH₃)-pyrimidine with X and YR₃ substituents]

| X | YR₃ |
|---|---|
| CH₃ | OCHCO₂C₂H₅<br>\|<br>CH₃ |
| CH₃ | S—CH₂CO₂CH₃ |
| CH₃ | SCH₂CH₂OCH₃ |
| OCH₃ | OCH₂CF₃ |

N-methyl compounds of this invention can be prepared in accordance with the procedures described above. For example, the methylation procedure of Equation 3 can be used as follows:

An equivalent amount of sodium hydride (50% mineral oil dispersion) is added to a solution of N-[[4-(2-methoxyethylthio)-6-methylpyrimidin-2-yl]aminocarbonyl]-2,5-dichlorobenzenesulfonamide in dimethylformamide under a nitrogen atmosphere. After hydrogen evolution ceases, an equivalent amount of dimethylsulfate is added. After stirring for 12 hours the reaction mixture is poured into a large volume of water. The resulting precipitate is filtered to yield N-[[4-(2-methoxyethylthio)-6-methylpyrimidin-2-yl]aminocarbonyl]-2,5-dichloro-N-methylbenzenesulfonamide.

Likewise, compounds of this invention wherein both of the urea nitrogens are methylated can be prepared by the procedure of Equation 4 as follows:

To 18 parts of N-[(2-chlorophenyl)sulfonyl]-N-methylcarbamyl chloride in 300 parts of tetrahydrofuran containing 10 parts of triethylamine is added 22 parts of 2-methylamino-4-(2,2,2-trifluoroethoxy)-6-methylpyrimidine. After stirring at reflux for 10 hours, the precipitated salts are filtered off and the filtrate is concentrated to yield N-[N-[4-(2,2,2,-trifluoroethoxy)-6-methylpyrimidin-2-yl]-N-methylaminocarbonyl]-2-chloro-N-methylbenzenesulfonamide.

By using an appropriate N-heterocyclic-N-aminocarbonylbenzenesulfonamide in the foregoing methylation procedure, the compounds of Table 5 can be prepared. Alternatively, by using an appropriate carbamylchloride and an appropriate methylaminoheterocycle with the above-described procedure, the compounds of Table 5 can be prepared.

Table 5-A

[Structure: R₅,R₄-phenyl-SO₂N(CH₃)-C(=O)-N(R₂)-heterocycle with X and YR₃]

| R₂ | R₄ | R₅ | X | YR₃ |
|---|---|---|---|---|
| H | Cl | H | CH₃ | SCH₂CH₂OCH₃ |
| H | Cl | H | CH₃ | OCH₂CF₃ |
| H | Cl | H | CH₃ | OCH₂CO₂CH₃ |
| H | Cl | 5-Cl | CH₃ | OCH₂CH₂CO₂C₂H₅ |
| H | NO₂ | H | CH₃ | OCH₂CH₂OC₂H₅ |
| H | NO₂ | H | CH₃ | SCH₂CH₂OC₂H₅ |
| H | NO₂ | H | CH₃ | OCHCO₂CH₃<br>\|<br>CH₃ |
| H | NO₂ | H | OCH₃ | S—CH₂CO₂CH₃ |
| H | Br | 5-Cl | OCH₃ | OCH₂CF₃ |
| CH₃ | CH₃ | H | CH₃ | SCH₂CH₂OCH₃ |
| CH₃ | Cl | H | CH₃ | OCH₂CO₂CH₃ |
| CH₃ | Cl | 5-Cl | OCH₃ | OCH₂CH₂OC₂H₅ |
| CH₃ | NO₂ | H | CH₃ | OCH₂CF₃ |

Table 5-A-continued

| R₂ | R₄ | R₅ | X | YR₃ |
|---|---|---|---|---|
| CH₃ | NO₂ | H | CH₃ | SCHCO₂C₂H₅<br>\|<br>CH₃ |

Table 5-B

[Structure: same as 5-A but with triazine heterocycle]

| R₂ | R₄ | R₅ | X | YR₃ |
|---|---|---|---|---|
| H | Cl | H | CH₃ | SCH₂CH₂OCH₃ |
| H | Cl | 5-Cl | CH₃ | OXCH₂CF₃ |
| H | NO₂ | H | CH₃ | OCH₂CO₂CH₃ |
| H | NO₂ | H | CH₃ | S—CH₂CO₂CH₃ |
| H | NO₂ | H | OCH₃ | OCHCO₂CH₃<br>\|<br>CH₃ |
| CH₃ | OCH₃ | H | CH₃ | SCH₂CH₂OCH₃ |
| CH₃ | S—CH₃ | H | CH₃ | S—CH₂CH₂OC₂H₅ |
| CH₃ | O↑SCH₃↓O | H | OCH₃ | OCH₂CH₂CH₂OCH₃ |
| CH₃ | NO₂ | H | CH₃ | OCH₂CF₃ |

By using an appropriately substituted N-methyl-N-phenylsulfonylthiocarbamyl chloride and an appropriately substituted 2-aminopyrimidine or 2-amino-1,3,5-triazine the compounds of Table 6 can be made in accordance with the procedure exemplified above.

Table 6-A

[Structure: R₅,R₄-phenyl-SO₂N(CH₃)-C(=S)-N(R₂)-pyrimidine with X and YR₃]

| R₂ | R₄ | R₅ | X | YR₃ |
|---|---|---|---|---|
| H | Cl | H | CH₃ | SCH₂CH₂OCH₃ |
| H | Cl | 5-Cl | CH₃ | OCH₂CF₃ |
| H | NO₂ | H | CH₃ | OCH₂CO₂CH₃ |
| H | NO₂ | H | CH₃ | S—CH₂CH₂OCH₃ |
| H | CH₃ | H | CH₃ | S—CH₂CO₂C₂H₅ |
| H | OCH₃ | H | OCH₃ | OCHCO₂C₂H₅<br>\|<br>CH₃ |
| CH₃ | Br | H | CH₃ | OCH₂CH₂OC₂H₅ |
| CH₃ | Cl | 5-Cl | CH₃ | SCHCO₂CH₃<br>\|<br>CH₃ |
| CH₃ | NO₂ | H | CH₃ | OCH₂CF₃ |
| CH₃ | NO₂ | H | OCH₃ | OCH₂CH₂CH₂OCH₃ |

Table 6-B $$R_5 \underset{R_4}{\diagdown} \text{-SO}_2\text{N}(\text{CH}_3)\text{-C}(=\text{S})\text{-N}(R_2)\text{-}\underset{N=YR_3}{\diagup N=X}$$

| R₂ | R₄ | R₅ | X | YR₃ |
|---|---|---|---|---|
| CH₃ | Cl | H | CH₃ | SCH₂CH₂OCH₃ |
| CH₃ | Cl | 5-Cl | CH₃ | OCH₂CO₂CH₃ |
| CH₃ | NO₂ | H | CH₃ | S—CH₂CH₂OCH₃ |
| CH₃ | NO₂ | H | CH₃ | S—CH₂CH₂CO₂CH₃ |
| CH₃ | CH₃ | H | OCH₃ | OCHCO₂CH₃<br>\|<br>CH₃ |
| H | Br | H | CH₃ | OCH₂CH₂OC₂H₅ |
| H | Cl | 5-Cl | CH₃ | OCH₂CF₃ |
| H | NO₂ | H | CH₃ | OCH₂CH₂CH₂OCH₃ |
| H | SCH₃ | H | OCH₃ | SCH₂CO₂C₂H₅ |

The compounds of Table 7 can be prepared by the aforesaid methylation reaction by using an appropriate N-[(1,3,5-triazin-2-yl)aminocarbonyl]-2-thiophenesulfonamide; N-[(pyrimidin-2-yl)aminocarbonyl]-2-thiophenesulfonamide; N-[(1,3,5-triazin-2-yl)aminothioxomethyl]-2-thiophenesulfonamide or N-[(pyrimidin-2-yl)-aminothioxomethyl]-2-thiophenesulfonamide. Alternatively, the compounds of Table 7 can be prepared in accordance with the above-exemplified procedure, using an appropriately substituted N-methyl-N-(2-thienylsulfonyl)carbamyl chloride or thiocarbamyl chloride and an appropriately substituted 2-aminopyrimidine or 2-amino-1,3,5-triazine.

Table 7-A

| R₂ | X | YR₃ |
|---|---|---|
| H | CH₃ | SCH₂CH₂OCH₃ |
| H | CH₃ | OCH₂CF₃ |
| H | OCH₃ | OCH₂CO₂CH₃ |
| H | OCH₃ | S—CH₂CH₂OC₂H₅ |
| H | CH₃ | O—CH₂CH₂CH₂OCH₃ |
| CH₃ | CH₃ | S—CH—CO₂C₂H₅<br>\|<br>CH₃ |
| CH₃ | CH₃ | O—CH₂CH₂CO₂CH₃ |
| CH₃ | CH₃ | OCH₂CH₂OC₂H₅ |
| CH₃ | CH₃ | OCH₂CF₃ |

Table 7-B

| R₂ | X | YR₃ |
|---|---|---|
| H | CH₃ | SCH₂CH₂OCH₃ |
| H | CH₃ | OCH₂CF₃ |
| H | CH₃ | SCH₂CH₂CH₂OCH₂ |
| H | OCH₃ | OCH₂CO₂CH₃ |
| H | OCH₃ | SCH₂CO₂CH₃ |
| CH₃ | OCH₃ | OCHCO₂C₂H₅<br>\|<br>CH₃ |
| CH₃ | CH₃ | OCH₂CH₂CO₂CH₃ |
| CH₃ | CH₃ | SCH₂CH₂OC₂H₅ |
| CH₃ | CH₃ | SCHCO₂CH₃<br>\|<br>CH₃ |

Table 7-B-continued

| R₂ | X | YR₃ |
|---|---|---|
| CH₃ | CH₃ | OCH₂CF₃ |

Table 7-C

| R₂ | X | YR₃ |
|---|---|---|
| H | CH₃ | OCH₂CH₂OC₂H₅ |
| H | CH₃ | OCH₂CF₃ |
| H | CH₃ | OCHCO₂CH₃<br>\|<br>CH₃ |
| H | O—CH₃ | OCH₂CF₃ |
| H | CH₃ | OCH₂CH₂CO₂CH₃ |
| H | CH₃ | SCH₂CH₂CH₂OCH₃ |
| CH₃ | CH₃ | S—CH₂CH₂OC₂H₅ |
| CH₃ | CH₃ | S—CH₂CH₂CO₂CH₃ |
| CH₃ | O—CH₃ | SCH₂CH₂OCH₃ |
| CH₃ | O—CH₃ | OCH₂CF₃ |

Table 7-D

| R₂ | X | YR₃ |
|---|---|---|
| H | CH₃ | SCH₂CH₂OCH₃ |
| H | OCH₃ | OCH₂CF₃ |
| H | CH₃ | OCH₂CO₂CH₃ |
| CH₃ | CH₃ | S—CH₂CH₂OC₂H₅ |
| CH₃ | OCH₃ | S—CH₂CO₂CH₃ |
| CH₃ | CH₃ | OCH₂CH₂CH₃OCH₃ |
| CH₃ | CH₃ | OCHCO₂C₂H₅<br>\|<br>CH₃ |

Formulations

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table 8.

Table 8

| | Weight Percent* | | |
|---|---|---|---|
| | Active Ingredient | Diluent(s) | Surfactant(s) |
| Wettable Powders<br>Oil Suspensions,<br>Emulsions | 20–90 | 0–74 | 1–10 |

Table 8-continued

|  | Weight Percent* | | |
|---|---|---|---|
|  | Active Ingredient | Diluent(s) | Surfactant(s) |
| (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active Ingredient plus at least one of a Surfactant or a Diluent equals 100 weight percent.

Lower or higher levels of active ingredient can be present, depending on the intended use and the physical properties of the compound. Higher ratios of surfactant to active ingredient are sometimes desirable, and are achieved by incorporated into the formulation, or by tank mixing.

Some typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084). Granules and pellets can be made by spraying the active material on preformed granular carriers or by agglomeration techniques. See J. E. Browning, "Agglomeration", Chemical Engineering, Dec. 4, 1967, pp. 147ff. and "Perry's Chemical Engineer's Handbook", 4th Ed., McGraw-Hill, New York, 1963, pp. 8–59ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, Col. 3, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

Unless indicated otherwise, all parts are by weight in the following examples.

EXAMPLE 4

Wettable Powder
N-[[4-(2,2,2-trifluoroethoxy)-6-methylpyrimidin-2-yl]aminocarbonyl]-2-nitrobenzenesulfonamide: 90%
dioctyl sodium sulfosuccinate: 0.1%
sodium ligninsulfonate: 1%
synthetic fine silica: 8.9%

The ingredients are blended and ground in a hammer-mill to produce particles almost all of which are below 100 microns in size. That material is sifted through a U.S.S. No. 50 screen and packaged.

EXAMPLE 5

Granule
wettable powder of Example 4: 10%
attapulgite granules (U.S.S. #20–40; 0.84–0.42 mm): 90%

A slurry of wettable powder containing 50% solids is sprayed onto the surface of attapulgite granules in a double-cone blender. The granules are dried and packaged.

EXAMPLE 6

Wettable Powder
N-[[4-(2-methoxyethoxy)-6-methylpyrimidin-2-yl]aminocarbonyl]-2-nitrobenzenesulfonamide: 40%
dioctyl sodium sulfosuccinate: 1.5%
sodium ligninsulfonate: 3%
low viscosity methyl cellulose: 1.5%
attapulgite: 54%

The ingredients are thoroughly blended and passed through an air mill to produce an average particle size under 15 microns, reblended, and sifted through a U.S.S. No. 50 sieve (0.3 mm opening) before packaging.

EXAMPLE 7

Granule
wettable powder of Example 6: 25%
gypsum: 64%
potassium sulfate: 11%

The ingredients are blended in a rotating mixer, and water is sprayed onto that blend so as to effect granulation. When most of the granules have reached 1.0 to 0.42 mm (U.S.S. #18 to 40 sieves) in size, they are removed, dried, and screened. Oversize material is crushed to produce additional material in the desired range. The resulting granules contain 10% of the active ingredient.

EXAMPLE 8

Wettable Powder
N-[[4-(2,2,2-trifluoroethoxy)-6-methylpyrimidin-2-yl]aminocarbonyl]-2-nitrobenzenesulfonamide: 80%
sodium alkylnaphthalenesulfonate: 2%
sodium ligninsulfonate: 2%
synthetic amorphorus silica: 3%
kaolinite: 13%

The ingredients are thoroughly blended after grinding in a hammer mill to produce particles essentially all of which are under 100 microns in size; the material is reblended, sifted through a U.S.S. No. 50 sieve and packaged.

EXAMPLE 9

Wettable Powder
N-[[4-(2-methoxyethoxy)-6-methylpyrimidin-2-yl]aminocarbonyl]-2-nitrobenzenesulfonamide: 65% dodecylphenol polyethylene glycol ether: 2%
sodium ligninsulfonate: 4%
sodium silicoaluminate: 6%
montmorillonite (calcined): 23%

The ingredients are thoroughly blended. The liquid surfactant is added by spraying on the solid ingredients in a blender. After grinding in a hammer mill produce particles almost all of which are below 100 microns in size, the material is reblended, sifted through a U.S.S. #50 sieve (0.3 mm opening) and packaged.

EXAMPLE 10

Oil Suspension
N-[[4-(2,2,2-trifluoroethoxy)-6-methylpyrimidin-2-yl]aminocarbonyl]-2-nitrobenzenesulfonamide: 25%
polyoxyethylene sorbitol hexaoleate: 5%
highly aliphatic hydrocarbon oil: 70%

The ingredients are ground together in a sand mill until the solid particles have been reduced to under about 5 microns. The resulting suspension may be applied directly, but preferably after being extended further with oils or emulsified in water.

EXAMPLE 11

Aqueous Suspension
N-[[4-(2-methoxyethoxy)-6-methylpyrimidin-2-yl]-aminocarbonyl]-2-nitrobenzenesulfonamide: 25%
hydrated attapulgite: 3%
crude calcium ligninsulfonate: 10%
sodium dihydrogen phosphate: 0.5%
water: 61.5%

The ingredients are ground together in a ball or roller mill until the solid particles have been reduced to sizes under 10 microns, and then packaged.

EXAMPLE 12

Extruded Pellet
N-[[4-(2,2,2-trifluoroethoxy)-6-methylpyrimidin-2-yl]aminocarbonyl]-2-nitrobenzenesulfonamide: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer milled and then moistened with about 12% water. The mixture is extruded in the form of cylinders about 3 mm in diameter which are cut to produce pellets about 3 mm long. The pellets may be used directly, after drying, or dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

Solution
N-[[4-(2,2,2-trifluoroethoxy)-6-methylpyrimidin-2-yl]aminocarbonyl]-2-nitrobenzenesulfonamide: 5%
dimethylformamide: 95%

The ingredients are combined and stirred to produce a solution, which can be used for low volume applications.

UTILITY

The compounds of the present invention are highly active herbicides. They have utility for broad spectrum pre- and/or post-emergence weed control in areas where complete control of all vegetation is desired, such as around fuel storage tanks, ammunition depots, industrial storage areas, oil well sites, drive-in theatres, parking lots, billboards, highway and railroad structures. By properly selecting rate and time of application, compounds of this invention may be used also to modify plant growth beneficially.

The precise amount of the compound of Formula I to be used in any given situation will vary according to the particular end result desired, the amount of foliage present, the weeds to be controlled, the soil type, the formation and mode of application, weather conditions, etc. Since so many variables play a role, it is not possible to state a rate of application suitable for all situations. Broadly speaking, the compounds of this invention are used at levels of about 0.005 to 20 kg/ha with a preferred range of 0.125 to 10 kg/ha. In general, the higher rates of application from within this range will be selected for adverse conditions or where extended persistence in soil is desired.

The compounds of Formula I may be combined with other herbicides and are particularly useful in combination with ureas, such as 3-(3,4-dichlorophenyl)-1,1-dimethylurea, 3-(3,4-dichlorophenyl)-1-methoxy-1-methylurea, and 1,1-dimethyl-3-($\alpha,\alpha,\alpha$-trifluoro-m-tolyl)urea; the triazines such as 2-chloro-4-(ethylamino)-6-(isopropylamino)-s-triazine; the uracils such as 5-bromo-3-sec-butyl-6-methyluracil; N-(phosphono-methyl)glycine; 3-cyclohexyl-1-methyl-6-dimethylamino-s-triazine-2,4(1H,3H)-dione, N,N-dimethyl-2,2-diphenylacetamide; 2,4-dichlorophenoxyacetic acid (and closely related compounds); 4-chloro-2-butynyl-3-3-chlorophenylcarbamate; diisopropylthiolcarbamic acid, ester with 2,3-dichloroallyl alcohol; diisopropyl-thiolcarbamic acid, S-(2,3,3-trichloroallyl) ester; ethyl-N-benzoyl-N-(3,4-dichlorophenyl)-2-aminopropionate, 1,2-dimethyl-3,5-diphenylpyrazolium methylsulfate; methyl 2-[4-(2,4-dichlorophenoxy)phenoxy]propanoate; 4-amino-6-tert-butyl-3-(methylthio)-1,2,4-triazin-5(4H)-one; 3-isopropyl-1H-2,1,3-benzothiodiazin(4)-3H-one 2,2-dioxide; $\alpha,\alpha,\alpha$-trifluoro-2,6-dinitro-N,N-dipropyl-p-toluidine; 1,1'-dimethyl-4,4'-bipyridinium ion; monosodium methanearsonate; and 2-chloro-2',6'-diethyl(methoxymethyl)acetanilide.

The activity of the compounds of this invention was discovered in greenhouse tests. The tests are described and the data resulting from them are shown below.
0=no effect
10=maximum effect
B=burn
C=chlorosis or necrosis
D=defoliation
E=emergence inhibition
G=growth retardation
H=formative effects
S=albinism
U=unusual pigmentation
6Y=abscised buds or flowers

TEST PROCEDURE A

Seeds of crabgrass (Digitaria spp.), barnyardgrass (Echinochloa crusgalli), wild oats (Avena fatua), cassia (Cassia tora), morningglory (Ipomoea spp.), cocklebur (Xanthium spp.), sorghum, corn, soybean, rice, and wheat, as well as nutsedge tubers (Cyperus rotundus), were planted in a growth medium and treated preemergence with a nonphytotoxic solvent solution of the compounds of Table 9. Other batches of seeds and tubers for all of the foregoing weed and crop plants were planted at the same time as controls. The control plantings were untreated; i.e., neither any compound nor any solvent was applied. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledonary leaves, rice with three leaves, wheat with one leaf, and nutsedge with three-five leaves were sprayed with a nonphytotoxic solvent solution of the compounds of Table 9. Other groups of all the same weed and crop plants were sprayed with the same nonphytotoxic solvent so as to provide control plants. Pre-emergence and postemergence treated plants and controls were mantained in a greenhouse for sixteen days, then all treated plants were compared with their respective controls and rated visually for response to treatment. The data in Table 9 indicate that certain of the compounds of this invention have utility for selective post-emergence weed control in wheat.

TABLE 9

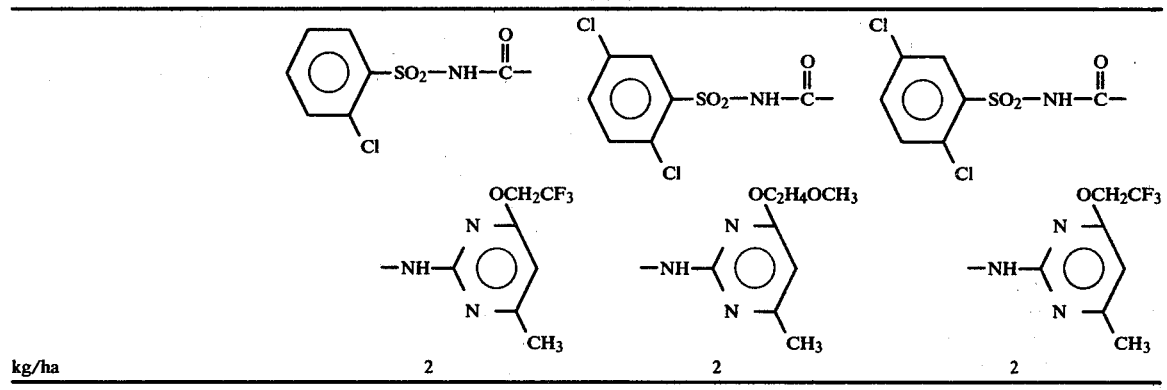

| kg/ha | 2 | 2 | 2 |
|---|---|---|---|
| POST EMERGENCE | | | |
| BUSH BEAN | 7D,8G,6Y | 3G,4C,6Y | 3C,4G,6Y |
| COTTON | 4C,9G | 2C,3H,6G | 2C,5G |
| MORNING GLORY | 10C | 10C | 7C |
| COCKLEBUR | 10C | 2C,7G | 3C,7G |
| CASSIA | 2C,7G | 2C,6G | 2C,7G |
| NUTSEDGE | 8G | 2C,7G | 2G |
| CRABGRASS | 1C,4G | 6G | 4G |
| BARNYARD GRASS | 2C,8H | 3C,7H | 2H |
| WILD OATS | 4G | 2G | 0 |
| WHEAT | 3G | 2G | 0 |
| CORN | 1C,5G | 3C,6G | 2C |
| SOYBEAN | 5H,7G | 9C | 2H,6G |
| RICE | 5G | 2C,5G | 1C |
| SORGHUM | 7G | 3C,7G | 0 |
| PRE EMERGENCE | | | |
| MORNING GLORY | 9G | 9G | 8G |
| COCKLEBUR | 8G | 8G | 7G |
| CASSIA | 9G | 9G | 4G |
| NUTSEDGE | 10E | 10E | 9G |
| CRABGRASS | 7G | 8G | 3G |
| BARNYARD GRASS | 8G | 3C,9H | 1C |
| WILD OATS | 4G | 6G | 0 |
| WHEAT | 5G | 8G | 3G |
| CORN | 9H | 9G | 2C,4G |
| SOYBEAN | 8H | 9H | 3H |
| RICE | 10E | 9H | 6G |
| SORGHUM | 9H | 2C,9G | 3G |

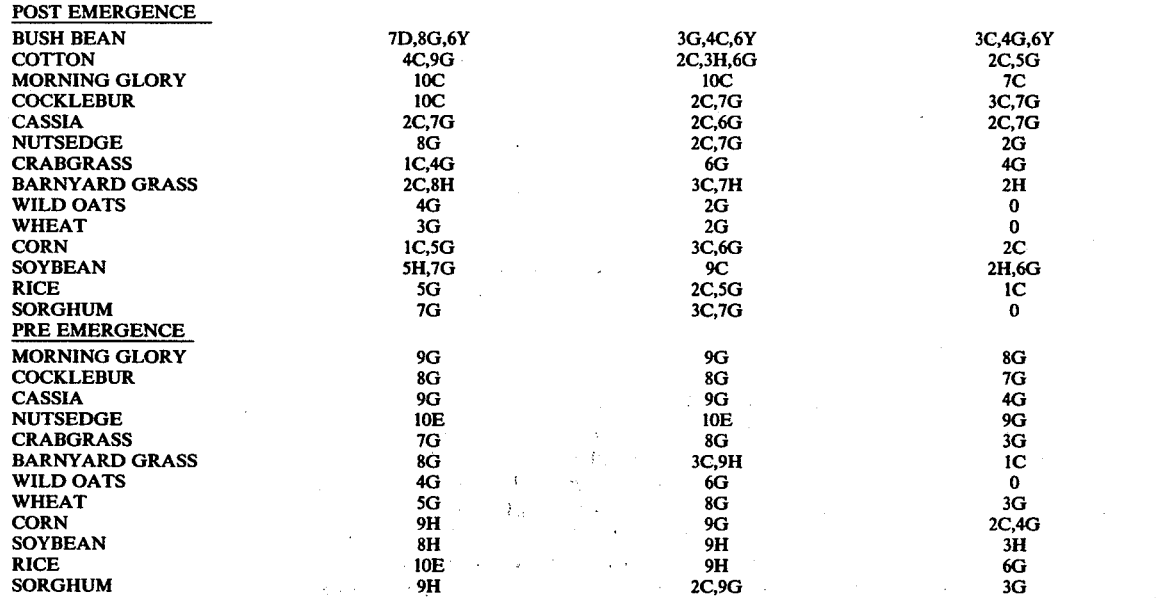

| kg/ha | 2 | 2 | 2 |
|---|---|---|---|
| POST EMERGENCE | | | |
| BUSH BEAN | — | — | 3C,8G,6Y |
| COTTON | 9C | 9C,5C | — |
| MORNING GLORY | 9C | 10C | 1C,9G |
| COCKLEBUR | 9C | 10C | 1C,7G |

TABLE 9-continued

| | | | |
|---|---|---|---|
| CASSIA | 9C | 10C | 8H |
| NUTSEDGE | 5C | 8C | 9G |
| CRABGRASS | 9C | 8C | 2C,8G |
| BARNYARD GRASS | 9C | 9C | 9H |
| WILD OATS | 9C | 9C | 0 |
| WHEAT | 9C | 9C | 0 |
| CORN | 10C | 10C | 2H,8G |
| SOYBEAN | 9C | 3C,8G | 2H,9G |
| RICE | 5C,8G | 5C,7G | 2C,8G |
| SORGHUM | 7C | 5C,9G | 9H |
| PRE EMERGENCE | | | |
| MORNING GLORY | 10E | 9G | 9G |
| COCKLEBUR | 8G | 9C | 9G |
| CASSIA | 9G | 9C | 8G |
| NUTSEDGE | 10E | 10E | 10E |
| CRABGRASS | 10E | 10E | 3G |
| BARNYARD GRASS | 9H | 9H | 9H |
| WILD OATS | 9C | 3C,8G | 6G |
| WHEAT | 9H | 9H | 6G |
| CORN | 10E | 9H | 2U,4G |
| SOYBEAN | 9H | 9H | 6H |
| RICE | 10E | 10E | 10E |
| SORGHUM | 9H | 9E | 9H |

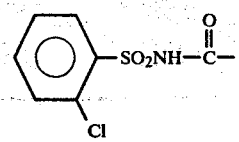 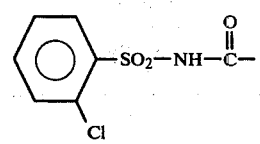

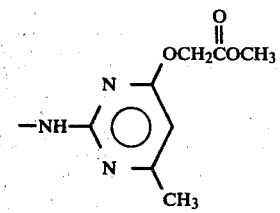 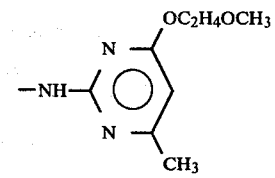

| kg/ha | 2 | 2 |
|---|---|---|
| POST EMERGENCE | | |
| BUSH BEAN | 8C,9G | 9C |
| COTTON | — | 2C,2H,9G |
| MORNING GLORY | 9C | 2H,7G |
| COCKLEBUR | 5C,8G | 1C,5G |
| CASSIA | 8C | 5C,9G |
| NUTSEDGE | 7G | 1C,8G |
| CRABGRASS | 6G | 10C |
| BARNYARD GRASS | 5C,9H | 10C |
| WILD OATS | 2C,8G | 2C,9G |
| WHEAT | 3C,7G | 2C,8G |
| CORN | 7U,9G | 2C,9G |
| SOYBEAN | 9C | 1C,9G |
| RICE | 3C,8G | 5C,9G |
| SORGHUM | 1U,8G | 2U,9G |
| PRE EMERGENCE | | |
| MORNING GLORY | 9H | 9G |
| COCKLEBUR | 8G | 10E |
| CASSIA | 8G | 10E |
| NUTSEDGE | 9G | 10E |
| CRABGRASS | 6G | 10E |
| BARNYARD GRASS | 9H | 3C,9H |
| WILD OATS | 2C,8G | 2C,9H |
| WHEAT | 9H | 9H |
| CORN | 10E | 10E |
| SOYBEAN | 9H | 9H |
| RICE | 10E | 10E |
| SORGHUM | 9H | 10C |

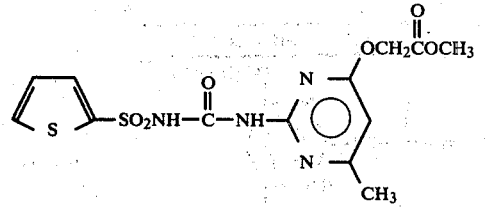

| kg/ha | 2 | 0.4 |
|---|---|---|

TABLE 9-continued

| POST EMERGENCE | | |
|---|---|---|
| BUSH BEAN | 4S,3H,8G | 3S,3H,8G |
| COTTON | 3C,9G | 2C,8G |
| MORNING GLORY | 10C | 10C |
| COCKLEBUR | 8G | 2C,7G |
| CASSIA | 2C,9G | 3C |
| NUTSEDGE | 1C,8G | 8G |
| CRABGRASS | 5G | 4G |
| BARNYARD GRASS | 2C,9H | 1C,4H |
| WILD OATS | 4G | 0 |
| WHEAT | 6G | 0 |
| CORN | 1C,9G | 2H,9G |
| SOYBEAN | 5C,9G | 9C |
| RICE | 5C,9G | 3C,9G |
| SORGHUM | 2C,9G | 1C,9G |
| PRE EMERGENCE | | |
| MORNING GLORY | 9G | 7G |
| COCKLEBUR | 7G | 6G |
| CASSIA | 7G | 8G |
| NUTSEDGE | 10E | 9G |
| CRABGRASS | 6G | 3G |
| BARNYARD GRASS | 2C,9H | 1C,8G |
| WILD OATS | 5G | 3G |
| WHEAT | 9G | 7G |
| CORN | 10E | 9G |
| SOYBEAN | 9G | 9G |
| RICE | 10E | 10E |
| SORGHUM | 9G | 9G |

TEST PROCEDURE B

Two bulb pans were filled with fertilized and limed Fallsington silt loam soil. One pan was planted with seeds of corn, sorghum, Kentucky bluegrass and several grassy weeds. The other pan was planted with seeds of cotton and soybeans, purple nutsedge tubers (*Cyperus rotundus*), and seeds of several broadleaf weeds. Seeds of the following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), giant foxtail (*Setaria faberii*), dallisgrass (*Paspalum dilatatum*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A smaller pot was also filled with prepared soil and planted with rice and wheat seeds. Another small pot was planted with seeds of sugarbeets. The above four containers were treated preemergence with non-phytotoxic solvent solutions of the compound of Table 10 (i.e., solutions of compounds were sprayed on the soil surface before seed germination). Duplicates of the above-described seeded containers were prepared without treatment and used as controls.

Twenty-eight days after treatment, the treated and control plants were evaluated and the data recorded as set forth in Table 10. Note that the data indicate that certain compounds of this invention are useful for weed control in crops such as soybeans and wheat.

TABLE 10
PRE-EMERGENCE ON FALLSINGTON SILT LOAM $$\text{PhSO}_2\text{-NH-C(=O)-NH-}\underset{\text{N}}{\overset{\text{N}}{\bigcirc}}\text{(OC}_2\text{H}_4\text{OCH}_3\text{, CH}_3\text{)}$$
(ortho-NO$_2$ on phenyl)

| Rate kg/ha | 1/16 | ¼ |
|---|---|---|
| Crabgrass | 10C | 10C |
| Barnyardgrass | 8G,8C | 10C |
| Sorghum | 9G,9C | 10C |
| Wild Oats | 4G,3C | 8G,5C |
| Johnsongrass | 8G,5C | 10C |
| Dallisgrass | 8G,5C | 10C |
| Giant Foxtail | 8G,6C | 10C |
| Ky. Bluegrass | 10C | 10C |
| Cheatgrass | 10C | 10C |
| Sugarbeets | 10C | 10C |
| Corn | 8G,8H | 10C |
| Mustard | 10C | 10C |
| Cocklebur | 2G | 7G |
| Pigweed | 10E | 10E |
| Nutsedge | 4G | 9G |
| Cotton | 5G,3H | 7G,5H |
| Morningglory | 5G | 8G |
| Cassia | 5G | 8G,9C |
| Teaweed | 5G,3C | 9G,8C |
| Velvetleaf | 5G | 9G,9C |
| Jimsonweed | 5G | 9G,9C |
| Soybean | 2G | 8G,5H |
| Rice | 9G,9C | 10C |
| Wheat | 7G,4C | 10C |

$$\text{PhSO}_2\text{-NH-C(=O)-NH-}\underset{\text{N}}{\overset{\text{N}}{\bigcirc}}\text{(OCH}_2\text{CF}_3\text{, CH}_3\text{)}$$
(ortho-NO$_2$ on phenyl)

| Rate kg/ha | 1/16 | ¼ |
|---|---|---|
| Crabgrass | 5G | 7G |
| Barnyardgrass | 8G,9C | 10C |
| Sorghum | 7G,8C | 10C |
| Wild Oats | 4G | 8G,5C |
| Johnsongrass | 8G,5C | 9G,5C |
| Dallisgrass | 7G | 8G,5C |
| Giant Foxtail | 7G,4C | 9G,8C |
| Ky. Bluegrass | 6G,3C | 8G,8C |
| Cheatgrass | 8G,3C | 8G,3C |
| Sugarbeets | 10C | 10C |
| Corn | 8G,8H | 9G,9H |
| Mustard | 10C | 10C |
| Cocklebur | 4G | 8G,5H |

TABLE 10-continued
PRE-EMERGENCE ON FALLSINGTON SILT LOAM

| | | |
|---|---|---|
| Pigweed | 10E | 10E |
| Nutsedge | 10E | 10E |
| Cotton | 7G | 7G |
| Morningglory | 7G | 8G,3H |
| Cassia | 6G | 8G,5C |
| Teaweed | 6G,3C | 8G,8C |
| Velvetleaf | 6G | 10C |
| Jimsonweed | 6G | 10C |
| Soybean | 7G,5H | 8G,5H |
| Rice | 9G,9C | 10C |
| Wheat | 4G | 7G,3C |

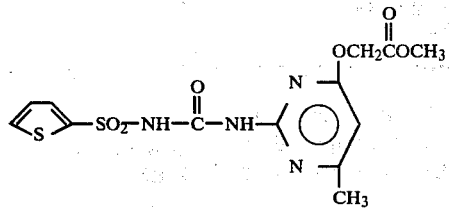

| Rate kg/ha | 1/16 | ¼ |
|---|---|---|
| Crabgrass | 0 | 3G |
| Barnyardgrass | 4G | 6G |
| Sorghum | 3G | 7G |
| Wild Oats | 2G | 4G |
| Johnsongrass | 0 | 7G |
| Dallisgrass | 0 | 0 |
| Giant Foxtail | 0 | 4G |
| Ky. Bluegrass | 0 | 5G |
| Cheatgrass | 0 | 5G |
| Sugarbeets | 8G,5C | 9G,8C |
| Corn | 3G | 7G |
| Mustard | — | — |
| Cocklebur | 6G | 5G |
| Pigweed | — | — |
| Nutsedge | 7G | 5G |
| Cotton | — | — |
| Morningglory | 5G | 5G |
| Cassia | — | — |
| Teaweed | — | — |
| Velvetleaf | — | — |
| Jimsonweed | 3G | 5G |
| Soybean | 5G | 7G,5H |
| Rice | 7G | 10C |
| Wheat | 0 | 0 |

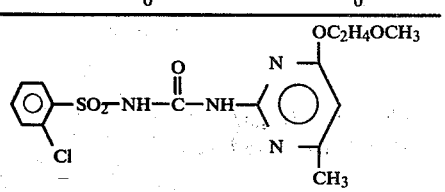

| Rate kg/ha | 1/16 | ¼ |
|---|---|---|
| Crabgrass | 0 | 5G |
| Barnyardgrass | 8G,8H | 10C |
| Sorghum | 8G,8H | 10C |
| Wild Oats | 5G,3H | 5G |
| Johnsongrass | 7G,5H | 10C |
| Dallisgrass | 4G | 10E |
| Giant Foxtail | 6G | 10C |
| Ky. bluegrass | 8G | 10E |
| Cheatgrass | 8C,5H | 10C |
| Sugarbeets | 4G | 8G,5H |
| Corn | 7G,5H | 10C |
| Mustard | 8G | 10C |
| Cocklebur | 0 | 0 |
| Pigweed | 10C | 10C |
| Nutsedge | 0 | 0 |
| Cotton | — | — |
| Morningglory | 0 | 3G |
| Cassia | 0 | 8G |
| Teaweed | 0 | 3G |
| Velvetleaf | — | — |
| Jimsonweed | 0 | 4G |
| Soybean | 0 | 2G |
| Rice | 7G,5H | 10C |

TABLE 10-continued
PRE-EMERGENCE ON FALLSINGTON SILT LOAM

| | | |
|---|---|---|
| Wheat | 5G | 7G |

TEST PROCEDURE C

Pots filled with Fallsington silt loam were planted to soybeans, cotton, alfalfa, corn, rice, wheat, sorghum, velvetleaf (*Abutilon theophrasti*), sesbania (*Sesbania exaltata*), cassia (*Cassia tora*), morningglory (*Ipomoea* spp.), jimsonweed (*Datura stramonium*), cocklebur (*Xanthium pennsylvanicum*), crabgrass (*digitaria* spp.), nutsedge (*Cyperus rotunda*), barnyardgrass (*Echinochloa crusgalli*), giant foxtail (*Setaria faberii*), and wild oats (*Avena fatua*). Approximately 2½ weeks after planting, the young plants and the soil around them were sprayed overall with the compounds of Table 11 dissolved in a nonphytotoxic solvent. Other groups of all the same weed and crop plants were sprayed with the same nonphytotoxic solvent so as to provide control plants. Fourteen days after treatment, all treated plants were compared with the nonphytotoxic solvent controls and visually rated for response to treatment to give the data presented in Table 11. The data indicate that several of the compounds tested by this procedure are useful for the post-emergence control of weeds in wheat.

TABLE 11
OVER THE TOP SOIL/FOLIAGE TREATMENT

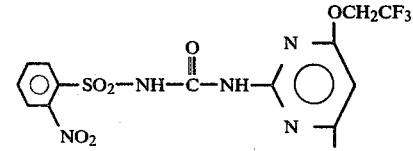

| Rate kg/ha | 1/16 | ¼ |
|---|---|---|
| Soybeans | 10C | 10C |
| Velvetleaf | 10G,7C | 10G,9C |
| Sesbania | 10C | 10C |
| Cassia | 5G,3C | 10G,7C |
| Cotton | 8G,5C | 10G,7C |
| Morningglory | 5G,5C | 10C |
| Alfalfa | 10G,7C | 10G,9C |
| Jimsonweed | 5G,3C | 10C |
| Cocklebur | 3G | 5G,3C |
| Corn | 10G,9C | 10G,9C |
| Crabgrass | 10G,7C | 10G,5C |
| Rice | 10G,4C | 10G,6C |
| Nutsedge | 4G | 7G |
| Barnyardgrass | 10C | 10G,6C |
| Wheat | 10G,4C | 10G,2C |
| Giant Foxtail | 10G,3C | 10G,6C |
| Wild Oats | 10G,3C | 10G,6C |
| Sorghum | 10G,8C | 10G,6C |

| Rate kg/ha | 1/16 | ¼ |
|---|---|---|
| Soybeans | 10C | 10C |
| Velvetleaf | 10C | 10C |
| Sesbania | 10C | 10C |
| Cassia | 10G,5C | 10G,6C |
| Cotton | 10G,3C | 8G,5C |
| Morningglory | 9G,3C | 10C |
| Alfalfa | 10G,9C | 10G,9C |
| Jimsonweed | 10C | 10C |
| Cocklebur | 10G,7C | 10G,7C |

TABLE 11-continued
OVER THE TOP SOIL/FOLIAGE TREATMENT

| | | |
|---|---|---|
| Corn | 10G,7C | 10G,9C |
| Crabgrass | 10G,6C | 10G,9C |
| Rice | 10G,7C | 7G,4C |
| Nutsedge | 7G | 7G |
| Barnyardgrass | 10C | 10G,7C |
| Wheat | 6G | 7G,2C |
| Giant Foxtail | 10G,5C | 10G,3C |
| Wild Oats | 10G,3C | 8G,2C |
| Sorghum | 10G,5C | 10G,9C |

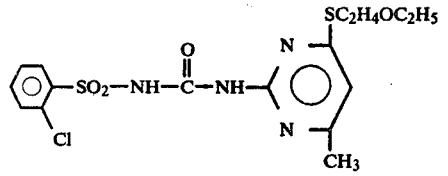

| Rate kg/ha | 1/16 | ¼ |
|---|---|---|
| Soybeans | 8G,2C | 10G,4C |
| Velvetleaf | 0 | 5G |
| Sesbania | 0 | 5G,2C |
| Cassia | 3H | 3G,5H |
| Cotton | 3G | 3G |
| Morningglory | 0 | 6G |
| Alfalfa | 0 | 7G |
| Jimsonweed | 0 | 7G,4C |
| Cocklebur | 0 | 3G,2C |
| Corn | 3G,2H | 8G,5H |
| Crabgrass | 0 | 3G |
| Rice | 0 | 0 |
| Nutsedge | 0 | 0 |
| Barnyardgrass | 5G | 8G |
| Wheat | 0 | 0 |
| Giant Foxtail | 0 | 3G |
| Wild Oats | 0 | 0 |
| Sorghum | 5G,3H | 7G,3H |

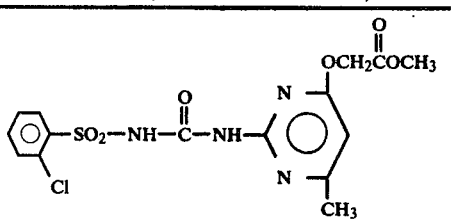

| Rate kg/ha | 1/16 | ¼ |
|---|---|---|
| Soybeans | 10G,6C | 10G,7C |
| Velvetleaf | 5G,2C | 10G,5H |
| Sesbania | 10G,5C | 10G,8C |
| Cassia | 10G,4C | 10G,6C |
| Cotton | 8G,2C | 10C |
| Morningglory | 6G | 8G,2C |
| Alfalfa | 4G | 10G,4C |
| Jimsonweed | 7G,2C | 9G,3H |
| Cocklebur | 3G | 5G |
| Corn | 7G | 8G |
| Crabgrass | 0 | 5G |
| Rice | 10G | 10G,2C |
| Nutsedge | 0 | 0 |
| Barnyardgrass | 10G | 10G,4C |
| Wheat | 0 | 7G |
| Giant Foxtail | 5G | 10G,3C |
| Wild Oats | 0 | 8G,3C |
| Sorghum | 10G | 10G,3C |

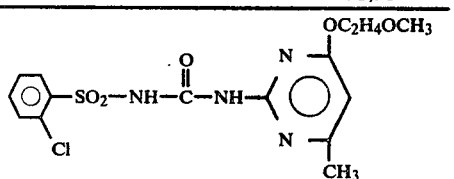

| Rate kg/ha | 1/16 | ¼ |
|---|---|---|
| Soybeans | 2G,3B | 5G,3B |
| Velvetleaf | 2G | 5G |
| Sesbania | 10G,2C | 10G,5C |
| Cassia | 0 | 5G |

TABLE 11-continued
OVER THE TOP SOIL/FOLIAGE TREATMENT

| | | |
|---|---|---|
| Cotton | 4G | 6G |
| Morningglory | 0 | 0 |
| Alfalfa | 5G | 5G |
| Jimsonweed | 2G | 4G |
| Cocklebur | 0 | 0 |
| Corn | 10G,3C | 10G,4C |
| Crabgrass | 3G | 4G |
| Rice | 7G | 5G,2C |
| Nutsedge | 0 | 3G |
| Barnyardgrass | 8G,3C | 10G,4C |
| Wheat | 8G,3C | 10G,3C |
| Giant Foxtail | 6G | 10G |
| Wild Oats | 6G | 10G,3C |
| Sorghum | 8G,2C | 10G,3C |

What is claimed is:

1. A compound, or an agriculturally acceptable salt thereof, which has the formula:

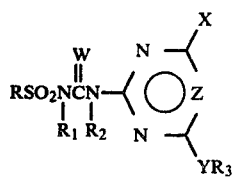

wherein
R is

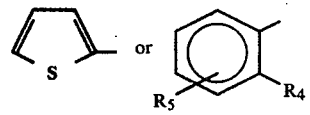

$R_1$ and $R_2$ are independently H or $CH_3$;
$R_3$ is $-CH_2CF_3$, $-CH_2CH_2OR_6$, $-CH_2CO_2R_6$, $$-\underset{CH_3}{\underset{|}{CH}}CO_2R_6,$$

$-CH_2CH_2-CH_2OR_6$ or $-CH_2CH_2CO_2R_6$;
$R_4$ is Cl, Br, F, $NO_2$, $CH_3$, $-OCH_3$, $CF_3$, or

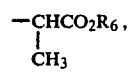

$R_5$ is H, Cl, Br, F, $CH_3$ or $-OCH_3$;
$R_6$ is $CH_3$ or $CH_2CH_3$;
n is 0, 1 or 2;
X is $CH_3$ or $-OCH_3$;
W and Y are independently O or S; and
Z is CH or N;
provided that
(a) when $R_3$ is $-CH_2CF_3$, Y is O; and
(b) when $R_3$ is $-CH_2CH_2OCH_3$ and either or both of $R_1$ and $R_2$ is $CH_3$, Y is S.

2. A compound of claim 1 wherein $R_1$ and $R_2$ are hydrogen and W is oxygen.

3. A compound of claim 2 wherein R is

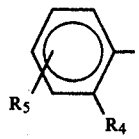

4. A compound of claim 3 wherein $R_5$ is H of Cl.
5. A compound of claim 4 wherein $R_4$ is Cl or $NO_2$.
6. A compound of claim 5 wherein $R_5$ is H.
7. A compound of any one of claims 1 through 6 inclusive wherein Y is O.
8. The compound of claim 1 which is N-[[4-(2-methoxyethoxy)-6-methylpyrimidin-2-yl]aminocarbonyl]-2-nitrobenzenesulfonamide.
9. The compound of claim 1 which is N-[[4-(2,2,2-trifluoroethoxy)-6-methylpyrimidin-2-yl]aminocarbonyl]-2-nitrobenzenesulfonamide.
10. A composition suitable for controlling the growth of undesired vegetation which comprises an effective amount of a compound of claim 1 and at least one of the following: surfactant, solid or liquid diluent.
11. a composition suitable for controlling the growth of undesired vegetation which comprises an effective amount of a compound of claim 2 and at least one of the following: surfactant, solid or liquid diluent.
12. A composition suitable for controlling the growth of undesired vegetation which comprises an effective amount of a compound of claim 3 and at least one of the following: surfactant, solid or liquid diluent.
13. A composition suitable for controlling the growth of undesired vegetation which comprises an effective amount of a compound of claim 4 and at least one of the following: surfactant, solid or liquid diluent.
14. A composition suitable for controlling the growth of undesired vegetation which comprises an effective amount of a compound of claim 5 and at least one of the following: surfactant, solid or liquid diluent.
15. A composition suitable for controlling the growth of undesired vegetation which comprises an effective amount of a compound of claim 6 and at least one of the following: surfactant, solid or liquid diluent.
16. A composition suitable for controlling the growth of undesired vegetation which comprises an effective amount of a compound of claim 7 and at least one of the following: surfactant, solid or liquid diluent.
17. A composition suitable for controlling the growth of undesired vegetation which comprises an effective amount of the compound of claim 8 and at least one of the following: surfactant, solid or liquid diluent.
18. A composition suitable for controlling the growth of undesired vegetation which comprises an effective amount of the compound of claim 9 and at least one of the following: surfactant, solid or liquid diluent.
19. A method for controlling the growth of undesired vegetation which comprises applying to the locus to be protected an effective amount of a compound of claim 1.
20. A method for controlling the growth of undesired vegetation which comprises applying to the locus to be protected an effective amount of a compound of claim 2.
21. A method for controlling the growth of undesired vegetation which comprises applying to the locus to be protected an effective amount of a compound of claim 3.
22. A method for controlling the growth of undesired vegetation which comprises applying to the locus to be protected an effective amount of a compound of claim 4.
23. A method for controlling the growth of undesired vegetation which comprises applying to the locus to be protected an effective amount of a compound of claim 5.
24. A method for controlling the growth of undesired vegetation which comprises applying to the locus to be protected an effective amount of a compound of claim 6.
25. A method for controlling the growth of undesired vegetation which comprises applying to the locus to be protected an effective amount of a compound of claim 7.
26. A method for controlling the growth of undesired vegetation which comprises applying to the locus to be protected an effective amount of the compound of claim 8.
27. A method for controlling the growth of undesired vegetation which comprises applying to the locus to be protected an effective amount of the compound of claim 9.

* * * * *